US011318318B2

(12) United States Patent
Boutaud

(10) Patent No.: US 11,318,318 B2
(45) Date of Patent: May 3, 2022

(54) METHODS OF MANUFACTURING A HERMETIC AND ISOLATING FEEDTHROUGH FOR AN ELECTRONIC DEVICE CASING, IN PARTICULAR MADE OF TITANIUM

(71) Applicant: MISTIC, Issy les Moulineaux (FR)

(72) Inventor: Bertrand Boutaud, Paris (FR)

(73) Assignee: MISTIC ( * ) Notice: Subject to any disclaimer, the term of this patent is extended or adjusted under 35 U.S.C. 154(b) by 751 days.

(21) Appl. No.: 16/151,317

(22) Filed: Oct. 3, 2018

(65) Prior Publication Data
US 2019/0099604 A1 Apr. 4, 2019

(30) Foreign Application Priority Data
Oct. 3, 2017 (FR) ...................................... 1759208

(51) Int. Cl.
A61N 1/37 (2006.01)
A61N 1/375 (2006.01)
H01G 2/10 (2006.01)
H01G 4/236 (2006.01)
H01G 4/35 (2006.01)
H02G 3/22 (2006.01)

(52) U.S. Cl.
CPC ........... A61N 1/375 (2013.01); A61N 1/3752 (2013.01); A61N 1/3754 (2013.01); H01G 2/103 (2013.01); H01G 4/236 (2013.01); H01G 4/35 (2013.01); H02G 3/22 (2013.01)

(58) Field of Classification Search
CPC .... A61N 1/375; A61N 1/3752; A61N 1/3754; H01G 2/103; H01G 4/236; H01G 4/35; H02G 3/22

USPC ........... 29/852, 846, 829, 825, 592.1, 25.41
See application file for complete search history.

(56) References Cited

U.S. PATENT DOCUMENTS

| 2007/0080360 | A1* | 4/2007 | Mirsky | .................. H05K 1/053 257/99 |
| 2011/0139484 | A1* | 6/2011 | Koester | .................. H01G 4/236 174/50.56 |
| 2011/0230937 | A1* | 9/2011 | Boutaud | .............. A61N 1/3754 607/62 |

(Continued)

Primary Examiner — Peter Dungba Vo
Assistant Examiner — Azm A Parvez
(74) Attorney, Agent, or Firm — CRGO Global; Steven M. Greenberg

(57) ABSTRACT

A device casing includes a wall having a metallic substrate and electrical connection of a feedthrough that includes a metal through-element made at least in a zone of isolation of the area of the feedthrough from the substrate material, in the form of an islet of closed contour, physically and electrically isolated from the substrate. An interface for coupling the through-element to the substrate provides the mechanical securing of the through-element to the substrate and the electrical isolation thereof and includes a peripheral lateral layer made of an electrically isolating material that surrounds the through-element over the whole periphery thereof and extends transversally through the thickness of the thinned area of the substrate. The substrate, the through-element and the lateral layer form a monolithically integrated unit, and the lateral layer provides essentially and directly both the mechanical securing and the electrical isolation between through-element and substrate.

12 Claims, 6 Drawing Sheets

(56) References Cited

U.S. PATENT DOCUMENTS

| | | |
|---|---|---|
| 2014/0020951 A1 | 1/2014 | Shah et al. |
| 2014/0367828 A1* | 12/2014 | Colonna ................ H01L 28/40 |
| | | 257/532 |
| 2015/0165218 A1 | 6/2015 | Markham et al. |
| 2016/0093531 A1* | 3/2016 | Harley .............. H01L 21/76898 |
| | | 438/667 |

* cited by examiner

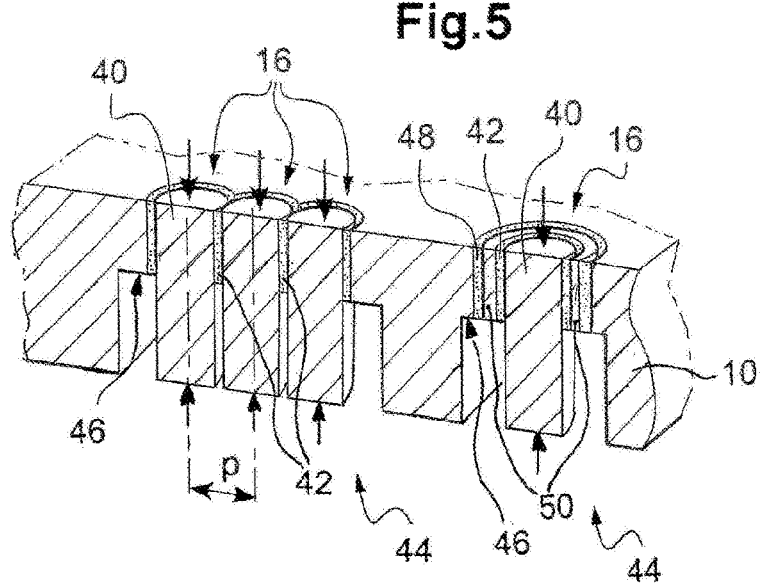
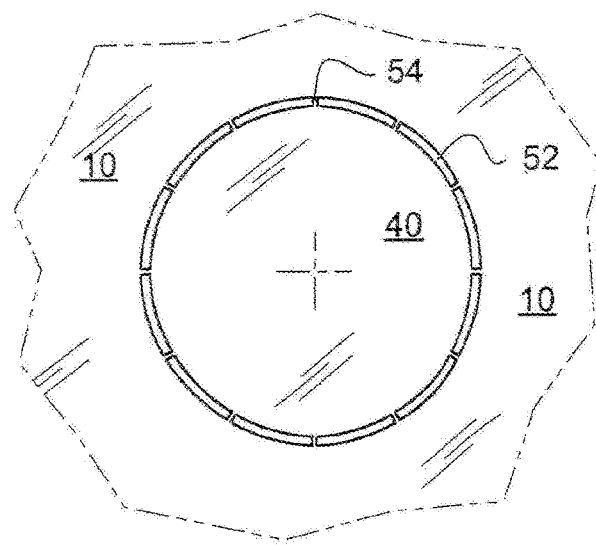
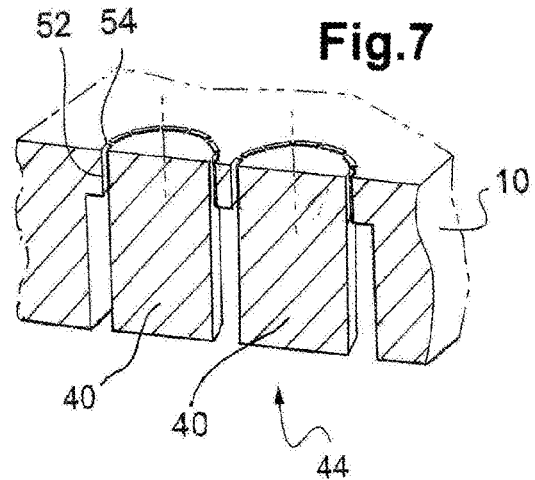

METHODS OF MANUFACTURING A HERMETIC AND ISOLATING FEEDTHROUGH FOR AN ELECTRONIC DEVICE CASING, IN PARTICULAR MADE OF TITANIUM

CROSS REFERENCE TO RELATED APPLICATIONS

This application claims priority under 35 U.S.C. § 119(a) to French Patent Application Serial Number 1759208, filed Oct. 3, 2017, the entire teachings of which are incorporated herein by reference.

BACKGROUND OF THE INVENTION

Field of the Invention

The invention relates to the technique for designing and manufacturing components or component parts called "feedthroughs", which are hermetic and electrically isolated passages for an electrical connection through a metal wall.

Description of the Related Art

In feedthroughs, a metal wall may be the casing of an electronic device. The feedthroughs then allow electrical connections to be made between the inner volume of the casing (inner side of the feedthrough), which for example contains electronic circuits, and an exposed surface of this same casing (outer side of the feedthrough). The electrical connection includes a conductive, metal through-element. The casing being metallic, and hence also conductive, it is necessary for an electrical isolation interface to be provided at the feedthrough between through-element and casing, the interface further providing a perfect hermeticity to preserve the tightness of the casing inner volume.

An example—not limitative—of such feedthroughs may be found in active medical devices, in particular those intended to be permanently implanted in the organism. Those devices are often designed as a generator composed of a metal casing, generally made of titanium, on which is mounted a connector head provided with accommodations for mechanically and electrically connecting to the generator casing one or several leads connected to remote electrodes.

The connection of the connector head contacts to the various electronic circuits contained in the casing involves making several feedthroughs in this casing, with, for each one, a pin intended to be connected, on the one hand, to a corresponding terminal of the connector head by its emerging end (outer side) and, on the other hand, to the electronic circuits by its opposite end (inner side) leading into the casing inner volume in which these circuits are located.

Such feedthroughs are described for example in European patent application publications EP 2 377 573 A1 and EP 2 873 437 A1. These feedthroughs may also be met in subcomponents of electronic, medical or other devices, such as batteries and capacitors. In the particular case of an implanted medical device, the feedthrough must not only isolate electrically the through-conductor (pin or other) of the metal casing, but must also be perfectly hermetic to avoid any penetration of fluid into the casing, and that, during the whole lifetime of the implanted device, typically during about ten years. The feedthrough is hence one of the key elements of the implantable medical devices, because it fulfils a double function of electrical current passage and of casing hermeticity.

Likewise, U.S. Pat. No. 7,310,216 to Greatbatch-Sierra and United States Patent Application Publication No. 2017/0203105 A1 describe such feedthroughs designed for active implantable medical devices and possibly incorporating, in addition to the electrical connections, structures for filtering or decoupling the electrical connections. The technologies implemented are however relatively complex and involve a multiplicity of successive steps, not only for making the feedthroughs but also for subsequently assembling each of them into the casing while guaranteeing the strongest and the most reliable possible mechanical connection.

Besides complexity, and consequently high cost, these technologies also suffer from a number of drawbacks resulting in particular from the fact that it is not possible to place the different adjacent feedthroughs as close as it would be desirable. Now, the trend to miniaturization and to electrical connection number increase, both in the medical device field or in many other fields, requires the center-to-center pitch between adjacent feedthroughs to be strongly reduced.

Notably, above-mentioned European patent application publications EP 2 377 573 A1 and EP 2 873 437 A1 describe a way to make a feedthrough by implementing technologies comparable to those used for manufacturing monolithically integrated circuits, including engraving a metallic substrate and depositing layers on the so-engraved substrate. This type of integrated feedthrough, which will be described in more detail hereinafter with reference to FIGS. 3 and 4, includes a through-element shaped into the substrate by engraving of the latter, and mechanically held thanks to an isolating layer previously deposited on the surface of the substrate. This upper holding and isolating layer covers both the substrate around the through-element and the through-element itself, which is then hung by the upper isolating layer—which provides the mechanical holding—at a position allowing a hollow interval to subsist over the whole peripheral contour thereof—which provides the electrical isolation from the remainder of the substrate.

However, to provide the required mechanical strength, the hanging by one or several upper layers requires the deposition of relatively thick layers (about 10 µm per layer) with respect to the conventional deposition methods used in the integrated-circuit technology, which turns out to be expensive. The thick layers may also generate a high level of mechanical stresses and a significant deformation of the substrate, which may make the manufacture complicated and have a negative effect on the reliability of the structure obtained.

Of course, to reinforce the structure, it is possible to subsequently add a material for filling the hollowed cavity, such as glue or resin. This stopgap nevertheless requires an additional step and hence increases the cost of manufacturing, and moreover leads to handling suspended structures, which are still rather fragile despite the plurality of support layers. Moreover, if one of the additional support layers is conductive, it is necessary to insert a small isolating wall between two adjacent feedthroughs, which penalizes the reduction of the center-to-center pitch between the feedthroughs.

Finally, a potential interaction between additional isolating and conductive layers may lead to a loss of electrical isolation over time. To guarantee the performances of the feedthrough during the whole lifetime of the device, it may then be necessary to add intermediate sub-layers that will limit the diffusions between neighbor layers, which increases even more the complexity of the structure and hence its cost of manufacturing.

Notably, United States Patent Application Publication Nos. US 2011/139484 A1 and US 2014/020951 A1 describe another technique for making a physical and electrical decoupling between the through-element and the metallic substrate that surrounds it and into which it is integrated, without anchoring bridge formed by an isolating layer added on the surface. This technique consists in monolithically integrating a central conductive islet, isolated from the remainder of the substrate over the whole thickness thereof by a peripheral lateral layer of isolating material filling the entirety of a previously hollowed-out circumferential groove, to define the shaped central islet into the substrate.

The implementation of this other technique nevertheless suffers from antagonist and irreconcilable technological and conceptual difficulties. Indeed, a component such as a feedthrough integrated into an implantable device casing requires a thickness of at least 100 to 150 µm so that the assembly operations between the two parts can be performed and to guarantee perfect hermeticity and mechanical stability to the obtained unit. More precisely, the assembly methods are most often based on a laser (or electrical) bonding that must typically be established through a minimum depth of 50 to 100 µm, with a thermally affected area that itself generally extends over 50 µm beyond the bonding.

To fulfil these requirements, the technique described by the two above-mentioned documents requires, on the one hand, to engrave a groove through a depth at least equal to the final thickness of the component, and on the other hand, to fill this groove with an electrically isolating material fulfilling the very strict hermeticity requirements of the implantable medical devices.

Now, about the latter point, it is well known that all the methods of depositing thick layers, thicker than a few micrometers, generate porosities and stratifications which are incompatible with very strict hermeticity requirements, and that, whatever the post-treatment performed, including those mentioned in the two above-mentioned documents.

Finally, for the mechanical holding of the central islet during the making of the feedthrough, the methods described by these two documents always provide to engrave an initially-blind groove, that hence leave, on the non-engraved fraction, an electrical continuity between the central islet and the remainder of the substrate. The suppression of this electrical continuity must be made by a final thinning down of the substrate over a depth higher than or equal to the non-engraved fraction.

This final thinning mechanism, which occurs over the whole surface area of the substrate, is de facto conceptually intrinsic to the techniques described by United States Patent Application Publications Nos US 2011/139484 A1 and US 2014/020951 A1. Moreover, for these techniques to be implementable, it is necessary to engrave micro-grooves over an opening of typically a few micrometers so that these latter can be filled by dense enough thin layers—and that, through a depth exceeding 100 µm. Now, the engraving technologies do not allow obtaining profiles with such small shape factors (ratio between opening and depth of engraving).

BRIEF SUMMARY OF THE INVENTION

The problem of the invention is to remedy these drawbacks and limitations of prior art by a new means of making a monolithically integrated feedthrough with a micrometric lateral vertical isolation that can guarantee a robust mechanical holding between two portions of a same substrate, by original mechanisms of mechanical holding of the islet during and after the process, with a particular sequence of manufacturing steps that, in particular, requires no general thinning down of the substrate after the steps of islet shaping and controlled oxidation, as in the case of the known techniques described hereinabove, through a thickness that may reach at least 100 to 150 µm, compatible with the making of feedthroughs integrated into an implantable device casing, and that, while guaranteeing perfect hermeticity and mechanical stability to the unit obtained.

The invention has also for object to allow the making of multiple, very close, feedthroughs, having an extremely reduced center-to-center pitch between adjacent feedthroughs, with consequently the possibility to highly miniaturize the device into which these feedthroughs are integrated and/or to gather the feedthroughs in an area of reduced extent, with a very high density of contacts.

The invention also allows, as will be seen, the addition to the feedthroughs of additional integrated components such as decoupling or filtering capacitors, RF antenna, etc., made in the same time as the feedthroughs.

For that purpose, the invention proposes a method of making a feedthrough such as that described by abovementioned United States Patent Application Publication No. US 2011/139484 A1, i.e. a hermetic monolithically integrated feedthrough with a lateral vertical isolation for the passage of an electrical connection through a metal wall of an electrical device.

Characteristically, the method of the invention includes the following steps:
a) obtaining a metallic substrate whose thickness corresponds to the transverse size of the wall including the feedthrough to be made;
b) thinning down the substrate, at least in a zone of isolation of the area of the feedthrough to be made;
c) shaping an islet into the substrate material, by hollowing out from the substrate material a through-trench extending transversally through the substrate thickness, right through the thinned region,
the through-trench extending transversally over the whole periphery of the islet with the exception of radial bridges of material holding the islet secured to the remainder of the substrate;
d) performing a controlled oxidation of the substrate material, including an oxidation of the lateral walls of the trench up to i) complete filling of the free inner volume of the trench by growth of the oxide in this free inner volume, and ii) complete oxidation of the material of the radial bridges; and
e) making at least one contact arrangement for the electrical connection directly on the islet.

According to various advantageous variants of implementation of this method:
the method includes successively a step of hollowing out, from a first face of the substrate, a blind trench extending transversally through a fraction of the substrate thickness, followed by the step b) of thinning down the substrate, from a second face opposite to the first face and facing the blind trench, over a sufficient depth to reach the blind trench and make the latter through-going;
at step b), the thinning down is made with a width varying as a function of the depth, increased near a first face of the substrate and reduced toward a second, opposite face of the substrate, near the radial bridges.

In an alternative mode of implementation of the concept of the invention, the method includes, for making the same type of feedthrough, the following successive steps:

a) obtaining a metallic substrate whose thickness corresponds to the transverse size of the wall including the feedthrough to be made;

b) shaping an islet into the substrate material, by hollowing out, from a first face of the substrate, at least one blind trench extending transversally through a fraction of the substrate thickness, the blind trench extending laterally over the whole periphery of the islet;

c) performing a controlled oxidation of the substrate material, including an oxidation of the lateral walls of the trench up to filling all or part of the free inner volume of the trench by growth of the oxide in this free inner volume;

d) hollowing out a peripheral groove from the substrate, from a second face opposite to the first face, the peripheral groove having radially such width and position that the groove, once hollowed out, reaches the oxidized blind trench facing it, hence electrically isolating the islet from the remainder of the substrate; and e) making at least one contact arrangement for the electrical connection directly on the islet.

Advantageously, at step e), the position of the hollowed-out peripheral groove shows a transverse offset of the peripheral groove contour with respect to the contour of the oxidized blind trench facing it, and it is provided, after the groove has been hollowed out, a step of selective isotropic engraving of the non-oxidized material of the substrate up to exposing the oxidized material of the trench, so as to hence electrically isolate the islet from the remainder of the substrate.

A variant of the above method includes the following steps:

a) obtaining a metallic substrate whose thickness corresponds to the transverse size of the wall including the feedthrough to be made;

b) shaping a first islet into the substrate material, by hollowing out, from a first face of the substrate, at least one blind trench extending transversally through a fraction of the substrate thickness, the blind trench extending laterally over the whole periphery of the first islet;

c) shaping a second islet into the substrate material, by hollowing out, from a second face of the substrate, opposite to the first face, at least one blind groove extending transversally through a fraction of the substrate thickness, the blind groove extending laterally over the whole periphery of the second islet, the contour of the second islet being close to the contour of the first islet;

d) performing a controlled oxidation of the substrate material, including an oxidation of the walls of the trench and of the groove through such a depth that, laterally, the oxidized area of the trench reaches the oxidized area of the groove, hence electrically isolating the first and second islets from the remainder of the substrate; and e) making a contact arrangement for the electrical connection directly on one and/or the other of the first and second islets.

In a particular mode of implementation of this method, step c) includes hollowing out, from the first face, at least a set of two concentric blind trenches laterally surrounding each respective blind groove on the second, opposite face.

According to advantageous implementations applicable to the various variants of the methods described herein-above:

the material of the metallic substrate and of the metal through-element is a material that is biocompatible, biostable and resistant to corrosion, in particular titanium;

the electrically isolating material of the peripheral lateral layer is an oxide of the material of the metallic substrate and of the through-element;

the coupling interface includes at least two concentric peripheral lateral layers made of an electrically isolating material;

in this latter case, the feedthrough may include a capacitor structure coupled to the electrical connection, the capacitor structure including three concentric lateral layers with, successively: a lower conductive layer formed in the substrate material, defining a first reinforcement for the capacitor; an intermediate layer made of an electrically isolating material, defining a dielectric of the capacitor; and an external conductive layer formed in the substrate material, defining a second reinforcement for the capacitor.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE SEVERAL VIEWS OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, wherein:

FIG. 5 is a cross-sectional view of the feedthroughs made by implementation of the invention, according to two possible exemplary embodiments.

FIGS. 6 and 7 are top and cross-sectional views, respectively, illustrating a first method according to the invention for making feedthroughs such as those illustrated in FIG. 5, at an initial step after engraving of the substrate and before oxidization of the latter.

DETAILED DESCRIPTION OF THE INVENTION

After a description of prior art, various examples of feedthroughs as well as two methods of making such feedthroughs using the teachings of the invention will be explained.

Feedthrough Structure with a Central Islet Held by a Bridge of Material

Figure 1:
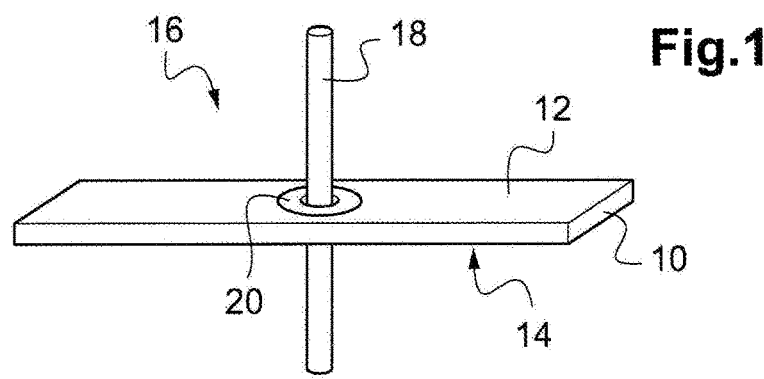
FIG. 1 is a schematic view of a feedthrough with the various elements of which it is made up.

FIGS. 1 to 4 illustrate a prior art structure. In FIG. 1 is illustrated the principle of a feedthrough, which is intended to allow the passage of an electric connection through an electrically conductive wall including a metallic substrate 10, typically made of titanium.

The metallic substrate 10 includes an upper face 12 and a lower face 14 (these two terms referring only to the presentation of the figures, without limitative connotation; it will be the same for the adjectives "outer" and "inner" used to denote respectively these two same sides with respect to a casing, the substrate 10 forms a wall of which). The feedthrough 16 includes an electrically conductive metal through-element 18, fully isolated from the remainder of the substrate 10 by an electrically isolating area 20, typically made of ceramic, fully surrounding the through-element 18 over the periphery thereof and extending right through the substrate 10, from the face 12 to the face 14.

The through-element 18 may in particular be consisted of a pin providing an electrical connection through the substrate 10. In other embodiments, the exposed surface of the through-element 18 is connected to conductive tracks extending over the surface of the substrate 10.

Figure 2:
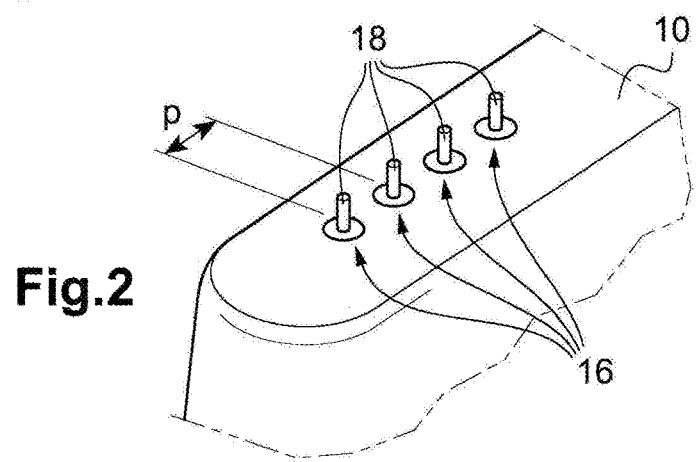
FIG. 2 is a perspective top view of an example of electronic device casing provided with several feedthroughs such as those of FIG. 1.

FIG. 2 illustrates an example of device whose casing outer wall is a metal wall, through which are made a plurality of feedthroughs 16.

These feedthroughs 16 include for example pins 18 for providing respective electrical connections, from the outside of the device, to corresponding terminals of internal circuits of the device. It will be understood that the center-to-center pitch p between adjacent pins is a significant element in the design of the device and that, in a number of configurations, it may be desirable to reduce as much as possible this center-to-center pitch value p.

Figure 3:
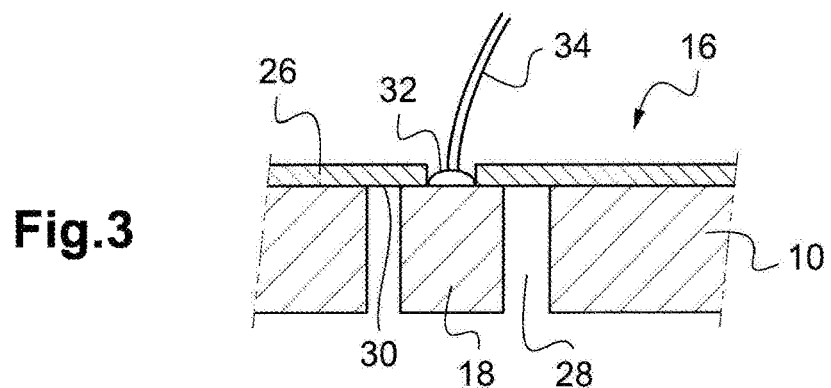
FIGS. 3 and 4 are cross-sectional views of a prior art feedthrough, according to respectively two variants differing by the way to make the contact arrangement on the through-element.

FIG. 3 illustrates a feedthrough structure as described in the above-mentioned EP 2 377 573 A1.

An upper outer isolating layer 26 is formed at the surface of the substrate 10, at least on the outer face thereof. This upper outer isolating layer 26 may be made in particular by oxidization of the titanium constituting the substrate 10 through a controlled depth, or by deposition of a layer of isolating material such as silicon oxide at the surface of the thickness of the substrate 10. The thickness of the upper outer isolating layer is for example of the order of 10 µm for a casing thickness of the order of 300 µm.

The structure of the feedthrough 16 further includes a conductive islet constituting the through-element 18. This conductive islet is arranged in the thickness of the substrate 10 by hollowing out a groove 28 into the whole thickness of the substrate 10, while leaving intact the isolating layer 26 so that the islet 18 can be supported by the bridge of material 30 formed by the isolating layer 26 between the area of the islet 18 and the remainder of the substrate 10. In the plane of the casing surface, the groove 28 is hollowed out along a closed contour so as to completely isolate, physically and hence electrically, the islet 18 from the remainder of the substrate 10, over the whole periphery thereof. The outer isolating layer 26 further constitutes a hermetic barrier between the two sides of the substrate, hence between the inside of the casing (the substrate forms the wall of which) and the external environment.

To provide the contact arrangement of the outer side, an opening 32 is formed into the outer isolating layer 26, right above the islet 18, so as to expose an area on which it will be possible to braze for example a wire 34 or a pin, which will be electrically connected to the central islet 18 of the feedthrough and electrically isolated from the remainder of the substrate. A connection of comparable type may be made on the other face of the substrate, on the inner side.

This known structure has the particularity that the central islet 18 is connected, and mechanically supported, only by the thin bridge or "membrane" of material 30 of the upper isolating oxide layer 26. This area, in particular the bottom of the groove 28, is particularly fragile and, during the method of manufacturing, defects or micro-fissures liable to weaken this bridge 30, already fragile due to its very low thickness, may appear.

Figure 4:
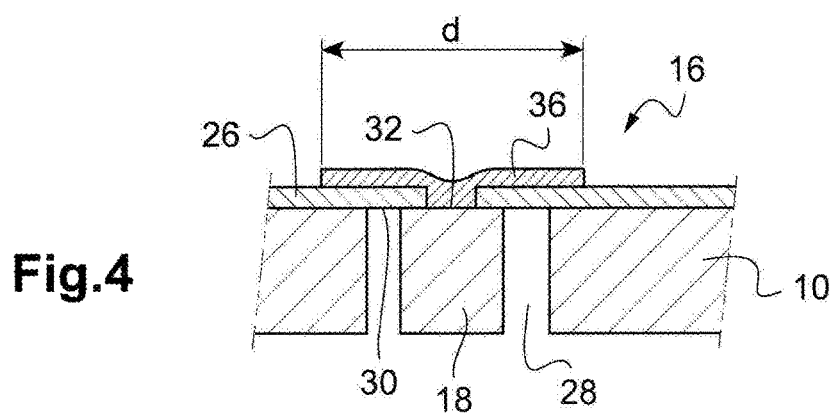

FIG. 4 illustrates an improvement proposed by the above-mentioned EP 2 873 437 A1 to compensate for this drawback.

This document teaches to deposit above the outer isolating oxide layer 26 an additional, isolating, outer layer 36, for example by depositing a plating of titanium or another material such as platinum, palladium, gold and the alloys thereof, and that over a thickness of the order of a few hundreds of nanometers to a few micrometers. This structure provides an improvement of the rigidity and the hermeticity of the bridge of material 30 mechanically connecting the islet 18 to the remainder of the substrate 10, due to the increase of the total thickness of material right above the groove 28.

However, this reinforced structure suffers from a number of drawbacks that remain, as already set out in introduction: increased number of steps in the manufacturing method with, correlatively, a higher cost of fabrication; necessity to deposit relatively thick layers (of the order of 10 µm per layer) to provide the mechanical strength with a risk of increased mechanical stress and of possible deformation of the substrate, etc.

It will also be noted that this improved technique has for consequence to increase relatively significantly the dimension d of the footprint of the feedthrough 16 on the substrate 10, which entails a relatively large center-to-center pitch between adjacent feedthroughs.

Feedthrough Structure with a Vertical Lateral Isolation

FIG. 5 is a cross-sectional view of the substrate 10 showing various types of feedthroughs with a vertical lateral isolation, liable to be made according to the teachings of the invention, with:

on the left, three adjacent feedthroughs 16, made on an area of the substrate having a reduced thickness;

on the right, a simple feedthrough 16, also made on an area of the substrate having a reduced thickness, with a structure providing a double isolation and/or allowing the potential integration of an integrated filtering or decoupling capacitive component.

In the figures, the vertical arrows schematize the positions at which the contact arrangements on the through-element of each feedthrough 16 will be made on either side of the substrate, according to techniques known per se that will be briefly described hereinafter, in particular with reference to FIGS. 10 and 11.

Each feedthrough 16 includes a metal through-element 40, which is an element formed in the substrate material and extending transversally through a thinned area, having a reduced thickness, of the substrate (wherein the total thickness of the substrate may vary, typically but without limitation, between 50 μm and 500 μm). Laterally, the through-element 40 is arranged as an element in the shape of an islet of closed contour, physically and electrically isolated from the substrate.

It will be noted that, in the present description, the term "transverse" indicates a direction corresponding to the substrate thickness, hence perpendicular to the surface of the latter, whereas a "lateral" direction will qualify a direction extending along the extent of the substrate, in other words a radial direction with respect to a transverse axis of the feedthrough.

As regards the closed peripheral contour of the islet defining the feedthrough element, this contour may be of any shape: circular, polygonal (rectangular) or indifferent, since, due to its closed character, it fully isolates the islet from the remainder of the substrate, both physically and electrically (the term "peripheral" having to be understood as qualifying a islet that is structurally separated and electrically isolated from the remainder of the substrate).

Moreover, the generating line defining the contour of the islet does not necessarily extend perpendicular to the substrate: for example, the contour may be a cylinder of revolution, but also any cylinder, or also a cone (see in particular FIG. 9), a pyramid, or of any shape.

The feedthrough further includes an interface for coupling the through-element 40 to the remainder of the substrate 10, which provides both the mechanical securing of this through-element to the substrate and the electrical isolation between through-element and substrate.

This coupling interface is not provided, as in prior art illustrated in FIGS. 3 and 4, by an upper anchoring bridge or membrane to which the through-element is hung in a recess of the substrate: in the present case, and characteristically, this interface is obtained by a peripheral lateral layer 42 made of an electrically isolating material, laterally surrounding the through-element 40 over the whole periphery thereof and extending transversally through a thinned portion, having a reduced thickness, of the substrate.

The manufacturing techniques that will be described below make it possible, in particular, to make a monolithically integrated unit including the substrate, the through-element and the lateral layer together. In this unit, the lateral layer provides, essentially and directly, a direct and lateral (mechanical) junction of the through-element 40 to the substrate 10, from which results both i) the mechanical securing of the through-element to the substrate and ii) the electrical isolation between the through-element and the substrate.

Very advantageously, the material of the peripheral lateral layer 42 is an oxide of the metal constituting the substrate 10, in particular titanium oxide $TiO_2$: indeed, the titanium and its oxide are materials that have the advantageous properties of biocompatibility, biostability and resistance to corrosion that make them particularly adapted to a very large number of applications, in particular for active medical devices in contact with corporeal tissues or fluids, especially implantable medical devices.

The controlled oxidation of a metal such as titanium is a well-known and mastered technique. In the case of the present invention, this oxidation may be made at a temperature of the order of 500 to 900° C., through a typical thickness of 0.1 to 15 μm.

As illustrated in FIG. 5, the feedthrough(s) 16 is(are) made through a portion 44 of the substrate having a reduced thickness, which has been thinned down from the lower face thereof (on the inner side of the casing) according to techniques that will be described hereinafter in particular with reference to FIG. 12.

Advantageously, as can be seen in the figures, this thinning down performed in the feedthrough area is a partial thinning, so that the metal through-elements 40 keep their initial thickness, the thinning concerning only the areas intended to become isolating areas. This local absence of thinning has for effect that the contact/connection zones remain at the same level as the substrate, both on the inner side and on the outer side of the latter.

In the example illustrated on the left in FIG. 5, a plurality of similar feedthroughs 16 are shown, made in the same way, with a center-to-center pitch p that may be very reduced due to the fact that the footprint in the lateral direction is that of the single through-element 40 with its lateral layer 42, without peripheral protrusion. Moreover, in this same example, the peripheral lateral layers 42 are adjacent to each other (i.e. an isolating oxide layer may be common to two adjacent feedthroughs in the area in which these latter are the closest), which makes it possible to reduce even more the center-to-center pitch p between adjacent feedthroughs.

Once the thinning of the portion 44 having a reduced thickness obtained, a recess or shoulder 46 is present between the peripheral lateral layer 42 and the lateral edge of the portion 44 having a reduced thickness. It will also be noted that, when a plurality of feedthroughs are made, these latter may be aligned, or not, the compactness of the feedthrough according to the invention making it possible to produce networks or grids of feedthroughs according to very varied configurations.

On the right in FIG. 5, an example of a simple feedthrough is shown, including two concentric peripheral lateral layers 42, 48 (the term "concentric" being understood in the broader meaning, that is to say that an outer layer 48 fully surrounds an inner layer 42, the contours of these layers being not necessarily coaxial, nor even circular).

Having several peripheral lateral layers makes it possible to maximize the electrical isolation between the through-element 40 and the remainder of the substrate 10.

This configuration also makes it possible to physically space apart the through-element 40 and the remainder of the substrate 10, which may be interesting in certain applications such as the radiofrequency applications, in which is it important to reduce the electromagnetic coupling between neighboring structures. In particular (and both for this embodiment and for the others), the through-element 40 can not only constitute a feedthrough, but also an isolated radiofrequency transmitting/receiving antenna, remote from the remainder of the substrate 10. In such a case, the element 40 will be able to adopt any known antenna geometric shape, such as loop, zigzag, spiral, fork, etc. Reference may be made in particular to the above-mentioned EP 2 873 437 A1, which describes such a type of RF component integrated to a substrate and connected to a monolithically integrated feedthrough made through this substrate.

This configuration including several peripheral lateral layers also makes it possible, by a suitable choice of the dimensions of these layers, to make an integrated filtering or decoupling capacitor structure that may be associated with the feedthrough: indeed, the alternation of the concentric metal/oxide/metal layers corresponds to a electrode/dielectric/electrode structure of a capacitor, the intermediate layer acting as a dielectric. This is, in the illustrated example, the case of the respective layers 40/42/50 and 50/48/10.

The parameters of this capacitor (capacitance, breakdown voltage) can be modulated by a suitable choice of the thickness of isolating material and of the size of the through-element (surface of the peripheral contour and length in transverse direction). These parameters may be chosen as a function of the technical objective: either to make a controlled coupling with the substrate (for example, for filtering purpose), or on the contrary to decouple as far as possible the feedthroughs from the substrate. In this latter case, it may in particular be advantageous to increase the number of concentric interfaces (as on the right in FIG. 5, where these concentric interfaces are two in numbers) because, in this case, the capacitances (undesirable) are electrically in series, which divides in proportion the whole coupling capacitance between the substrate 10 and the main through-element 40, in particular when the latter also provides an antenna function. Another possibility consists in maximally reducing the fraction of thickness of the thin trenches and not filling them. The free residual volume of the oxidized grooves then provides a greater capacitive decoupling between the through-islet and the remainder of the substrate. These micro-cavities may be let free, or filled by later deposition of another material so as to rigidify the structure. Advantageously, in the case in which the lowest possible electrical capacitance is desired, the material for the optional later filling may be chosen so as to have a lower dielectric constant than that of the oxide.

First Exemplary Method According to the Invention for Making a Feedthrough Structure with a Vertical Lateral Isolation It will now be described various methods according to the invention for obtaining feedthrough structures such as those described hereinabove, having the particular following characteristics:

monolithically integrated structure with a conductive central islet coming from the initial substrate;

engraving, on each substrate face, with:

on one face (the lower face in the figures), an engraving level making it possible to hollow out a wide access, with an opening typically included between 25 and 300 µm in the lateral direction, through a significant depth, typically higher than 80% of the initial thickness of the substrate in the transverse direction (the total thickness of the substrate being, typically but without limitation, included between 50 µm and 500 µm), and on the other face (the upper face in the figures), an engraving level making it possible to produce ultra-thin trenches, with an opening typically included between 0.1 and 15 µm in the lateral direction, through a reduced depth, typically of 1 to 50 µm in the transverse direction;

a lateral vertical and circumferential isolation of the islet with respect to the substrate thereof, through a fraction of this substrate thickness (preferably only in a zone of isolation of the area of the feedthrough to be made), the isolation being obtained by an oxidation of the substrate at the ultra-thin trenches; and potential additional plating operations allowing a contact arrangement of better quality.

As will be seen, the so-made feedthroughs solve the triple problem of mechanical holding of the central islet, electrical isolation thereof with respect to the remainder of the substrate, and final hermeticity and mechanical strength of the component.

A first method characteristic of the present invention is illustrated in FIGS. 6 to 12.

As illustrated in FIGS. 6, 7 and 8(a), a thin through-trench 52 is engraved into a thinned area 44, having a reduced thickness, of the substrate. More precisely, the substrate 10 is hollowed out through the whole thickness of this thinned area 44, the contour of the trench 52 laterally defining a central islet corresponding to the through-element 40 of the feedthrough to be made.

The thin through-trench 52 extending through the whole thickness of the thinned area 44, right through the latter, so as to be able to keep the central element 40 in place, it is provided to leave thin radial bridges 54 of non-engraved material. The number and configuration of these bridges or arms of non-engraved material may be included between 1 and a number as high as desirable, wherein these bridges can be symmetrical or not, and regularly distributed or not. By the way, it will be noted that the reduced thickness of the area 44 makes it possible to reduce the length in the transverse direction of the bridges of material 54.

The hollowing out of the thin through-trench 52 has hence made possible to shape the central islet corresponding to the through-element 40, this later being held in place by the bridges of material 54. This situation corresponds to that of FIG. 8(a).

At this step, the central element is held secured to the remainder of the substrate by the bridges 54, but it is not electrically isolated from the substrate because the bridges leave a conductive path. There is not either any hermeticity through the structure between the central element 40 and the remainder of the substrate 10, because the engraved sectors of the thin trench 54 leave an open free inner volume, visible in particular on the enlarged representation of FIG. 8(a).

Figure 8:
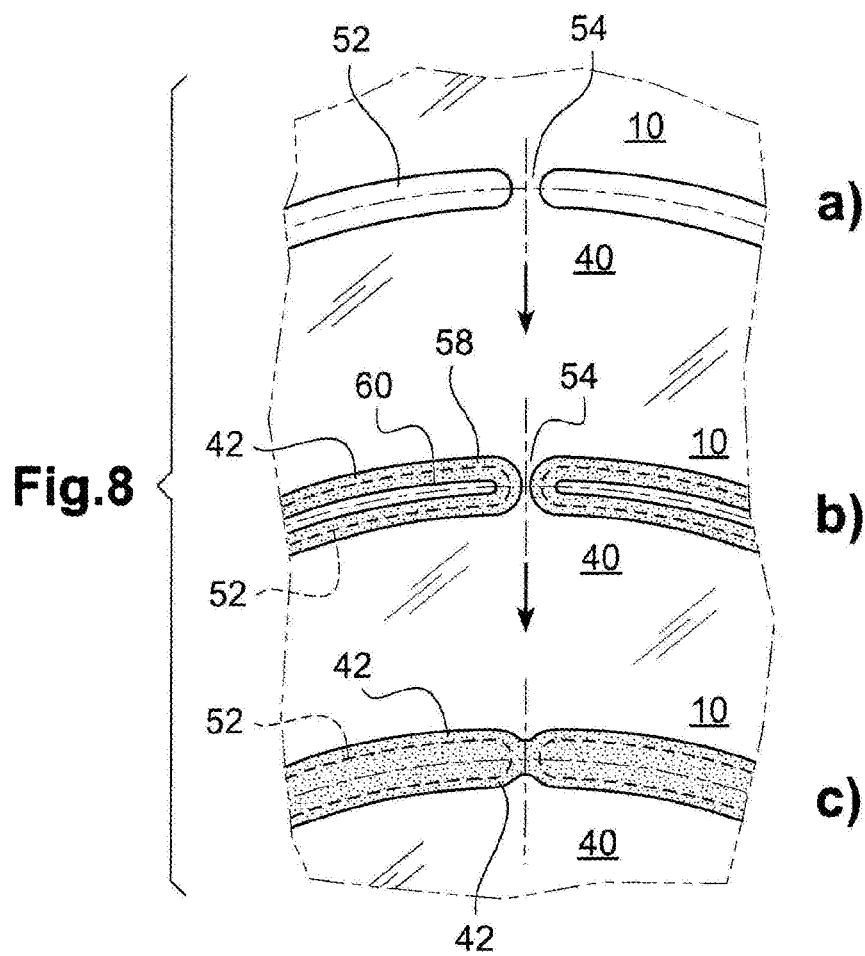
FIG. 8 is a top view illustrating the successive steps (a) to (c) of the oxidization step of the first method according to the invention, at one of the bridges of material visible in FIGS. 6 and 7.
Figure 9:
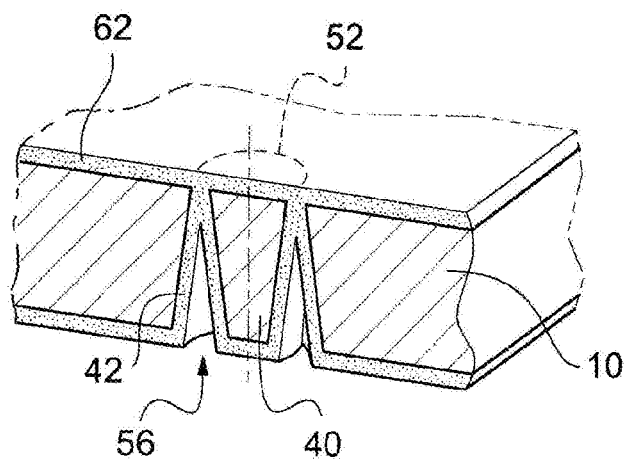
FIG. 9 is a cross-sectional view illustrating a variant of implementation of the method of the invention, after full completion of the oxidization step.

The following step, illustrated in FIGS. 8(b), 8(c) and 9, consists in making simultaneously the electrical isolation and the hermeticity of the central element 40 by a step of controlled-thermal oxidation of the substrate.

This step will produce, concurrently:

in depth, the growth of a front of isolating oxide consuming the metal of the substrate (that of the central element 40 as well as that of the remainder of the substrate 10), as illustrated in 58 in FIG. 8(b), where the initial place of the trench before oxidation is represented in dotted line in 52; and at the surface, the growth of a thickness of oxide on the walls of the thin trench 52, as illustrated in 60 in FIG. 8(b).

The continuation of the controlled oxidation will entail a progressive filling of the free inner volume remaining between the two opposite walls of the trench 52, up to the complete filling of this free volume, as illustrated in FIG. 8(c).

Moreover, the peripheral size of the linking arms 54 has been chosen small enough so that, once the phase of complete filling completed, the metal of the bridge of material 54 is entirely transformed into oxide, as also illustrated in FIG. 8(*c*). The two opposite fronts on either side of the bridge of material 54 have joined each other, hence electrically isolating the central element 40, and making it hermetic, relative to the remainder of the substrate 10.

FIG. 9 illustrates the result obtained in a variant of implementation in which, in cross-sectional view, the trench 52 hollowed out into the area 44 having a reduced thickness is not a trench of constant width, in other word a trench with parallel walls (as in the case illustrated in FIG. 7), but a trench of variable width, with non-parallel faces spacing apart from each other towards one of the substrate faces. This non-parallelism may in particular be introduced by the manufacturing method that generates an angle of penetration. The filling of the trench is then made over only a portion of the substrate thickness, chosen so as to provide the required level both of mechanical securing of the central element 40 to the substrate 10 and of electrical isolation of this through-element 40 with respect to the substrate 10. If the mechanical strength is not sufficient, the remaining cavity 56 may be filled by deposition of a third-party material, isolating or conductive.

The following step consists in making an electrical connection arrangement on the central element 40.

Indeed, the latter is electrically isolated from all sides, in particular by the upper oxide layer 62, and likewise on the opposite side by the lower oxide layer. It is hence necessary to make, at the through-element 40, an electrical continuity between the two faces of the substrate to form the electrical connection of the feedthrough.

The electrical connection arrangement (in this embodiment as in all the others) may be made on either one of the two faces—upper and lower—of the central through-element 40, with transfer or deposition of a conductive connection element (added wire, track on the surface of the substrate, etc.) intended to provide an electrical connection with distant elements, circuits or components located on either side of the substrate, in the same way as, for example, the feedthrough pins of the prior art.

But the electrical connection arrangement may be made on only one face of the through-element, the other face of the through-element being a directly usable active face, to constitute for example a surface electrode applied on one face of a device casing, or also on a sensor integrated to a device. This configuration is particularly advantageous for making an implantable device in which this surface electrode is intended to come into contact with a tissue of the patient into whom the device is implanted.

In all the cases, it is advisable to make exposed or leave exposed each of the upper and lower faces of the central through-element 40.

A first solution consists, before the oxidation, in depositing an oxidation inhibitor material such as, for example, titanium nitride, silicon nitride, tungsten, platinum, niobium or palladium, or any combination of these materials, over a thickness of a few tens to a few hundreds of nanometers, in the areas of the substrate surface in which it is desired to see the oxide grow. The electrical contact is then directly obtained after oxidation and elimination of the inhibitor layer, with possibly later deposition of an additional layer of a metallic material such as gold, platinum, palladium, niobium, iridium, or any combination of these materials.

Figure 10:
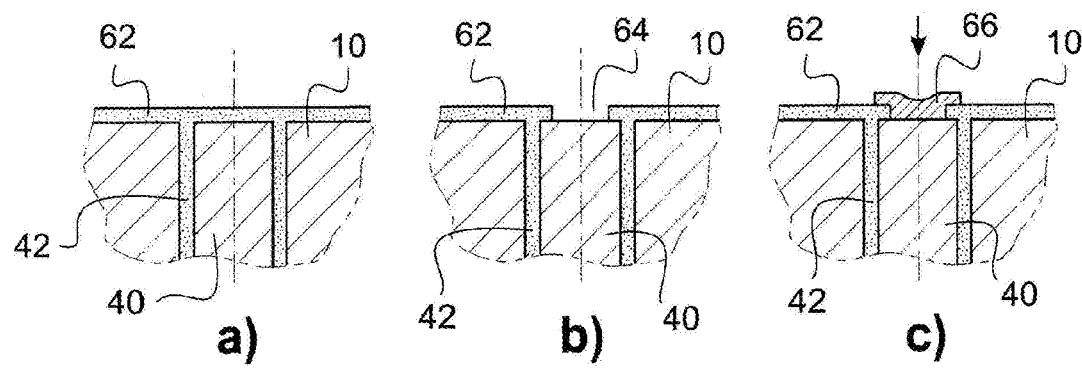
FIG. 10 is a cross-sectional view illustrating the successive steps (a) to (c) of making an electrical contact on the through-element, according to a first possible technique of contact arrangement.

Another solution, illustrated in FIG. 10, consists, after completion of the oxidation (FIG. 10(*a*)), in eliminating locally the oxide layer, for example by plasma or laser engraving, up to make the surface of the metallic material of the central element 40 exposed, as illustrated in 64 in FIG. 10(*b*).

The so-exposed electrical contact zone may, here again, be optimized by deposition, as illustrated in 66 in FIG. 10(*c*), of an additional metal layer made of a material such as gold, platinum, palladium, niobium, iridium or any combination of these materials. This additional metal layer may, laterally, either be confined to the area 64 without oxide, or protrude from the latter and cover the oxide beyond the periphery of the zone 64 (as illustrated in FIG. 10(*c*)).

Figure 11:
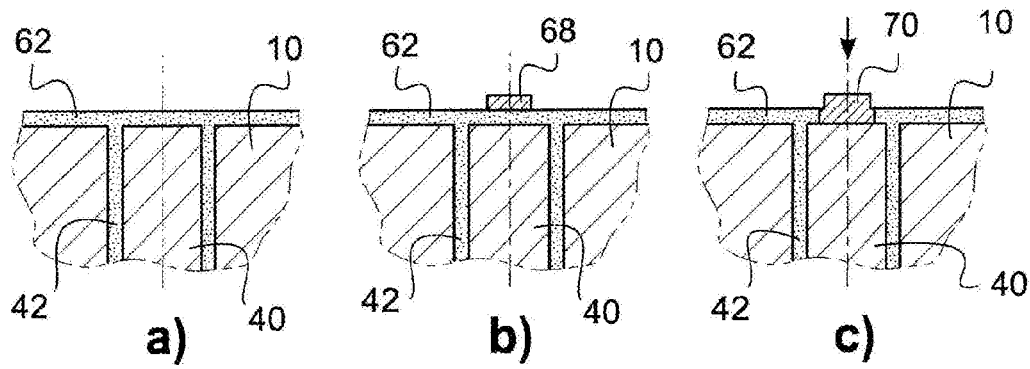
FIG. 11 is a cross-sectional view illustrating the successive steps (a) to (c) of making an electrical contact on the through-element, according to a second possible technique of contact arrangement.

Still another possibility of making the contact arrangement is illustrated in FIG. 11.

After the step of oxidizing the substrate (FIG. 11(*a*)), a layer of a suitable material, such as gold, platinum, palladium, niobium, iridium or any combination of these materials, is deposited above the zone in which it is desired to make the contact, as illustrated in 68 in FIG. 11(*b*). A heat treatment then generates a diffusion of this material in the oxide, as illustrated in 70 in FIG. 11(*c*), which has for effect to make this oxide conductive in the underlying zone.

These different techniques of making a contact arrangement are known per se and won't be described in more detail. They may be implemented in the same way on the other side of the substrate, so as to define an electrical continuity between the two faces, inner and outer, of the through-element and to hence make the electrical connection (or each electrical connection) of the feedthrough.

Figure 12:
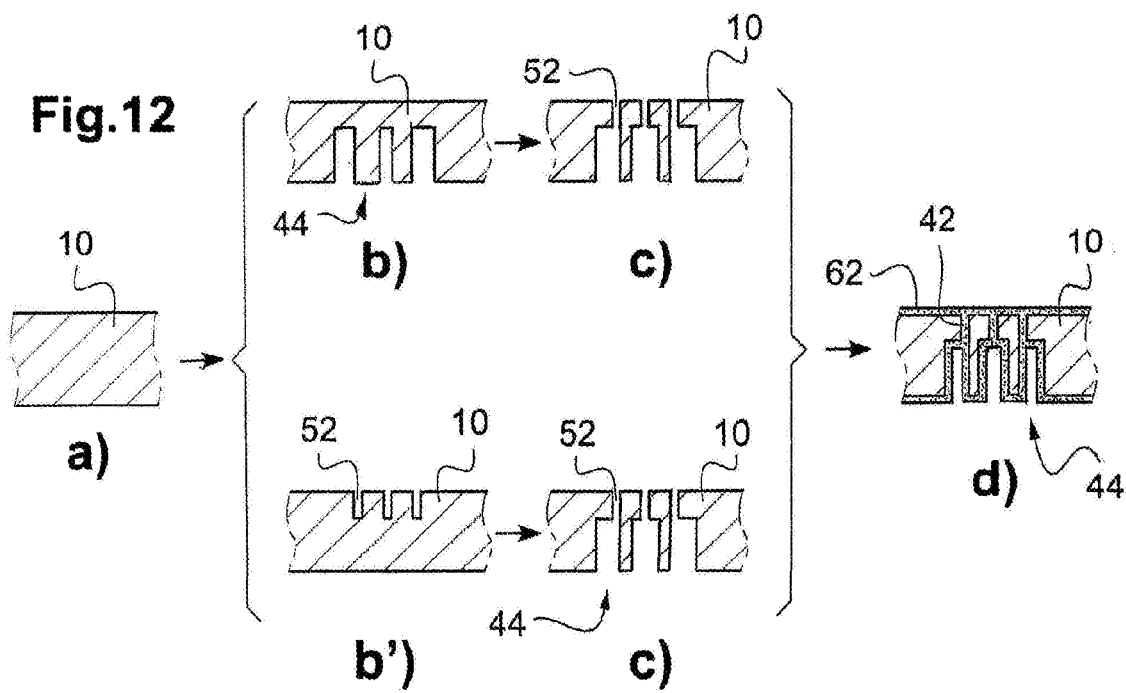
FIG. 12 is a cross-sectional view illustrating the various steps (a) to (d) of making a feedthrough by the first method according to the invention, according to two possible variants for thinning down the substrate in the feedthrough area.

FIG. 12 schematically illustrates, in particular, the making of the area 44 of the substrate having a reduced thickness, according to two possible variants:

in a first variant, the substrate is first thinned down in the area 44 to provide it with a reduced thickness, then the trench 52 is made as described hereinabove, i.e. by hollowing out a thin through-trench (FIGS. 12(*a*) to 12(*c*)) opening into the lower face of the thinned area 44;

in a second variant, a thin blind trench is hollowed out into the substrate, through a fraction of the thickness thereof, then, in order to obtain the area 44 having a reduced thickness, the substrate is thinned down over a sufficient depth to reach the thin blind trench 52 that had been hollow out from the other side of the substrate and hence make this latter through-going (FIGS. 12(*a*), 12(*b'*) et 12(*c'*)).

These steps according to either one of the variants are then followed with the step of oxidizing the substrate (FIG. 12(*d*)) making it possible to obtain the desired structure for making the isolation of the feedthroughs in the area 44 of the substrate having a reduced thickness.

Second Exemplary Method According to the Invention for Making a Feedthrough Structure with a Vertical Lateral Isolation It will now be described, with reference to FIGS. 13 to 16, a second method according to the invention for obtaining the monolithically integrated feedthrough structure whose characteristics have been described hereinabove.

Figure 13:
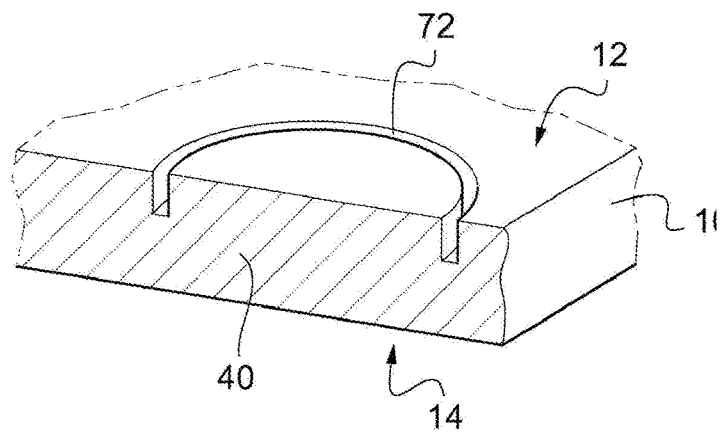
FIGS. 13 to 16 are cross-sectional views illustrating the different successive steps of a second method according to the invention of making a feedthrough.

The first step, illustrated in FIG. 13, consists in shaping an islet (corresponding to the through-element of the feedthrough to be made) by hollowing out from the substrate material, from a first face of the latter, for example the upper face 12, a thin blind trench 72 extending transversally through a fraction of the thickness of the substrate 10. Laterally, this thin trench extends over the whole periphery of the central islet 40—that is to say that the trench 72 does not leave bridges of material, unlike the thin trench 52 illustrated in FIG. 6 of the preceding method.

Figure 14:
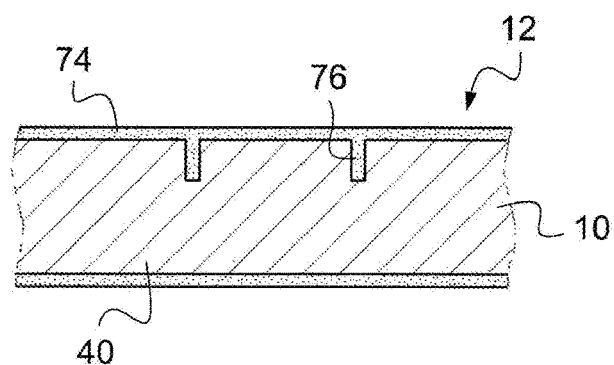

The following step, illustrated in FIG. 14, consists in performing a controlled oxidation of the substrate material, including an oxidation of the lateral walls of the thin trench up to filling all or part of the free inner volume of the latter by oxide growth.

At the end of this oxidation step, the substrate includes on either one of its faces a layer of oxide coating 74 (typically of a few micrometers of thickness) extending, on the side of the upper face 12, along the thin trench 76 that is fully filled (as illustrated in FIG. 14) or only partially filled. In the case of a partial filling, the filling may be optionally made complete by the later deposition of an isolating or conductive filling layer, so as, in particular, to mechanically reinforce the structure.

Figure 15:
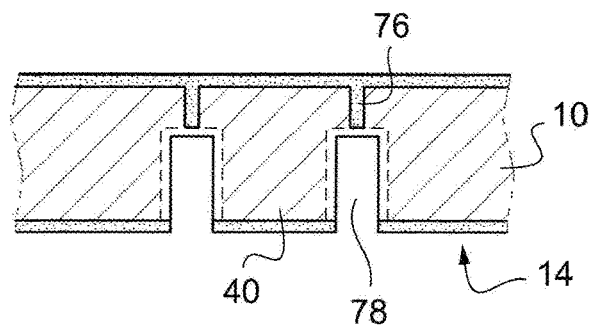

The following step, illustrated in FIG. 15, consists in hollowing out a peripheral groove 78 from the other face of the substrate, i.e. the lower face 14 in the illustrated example. This peripheral groove 78 may be hollowed out through a depth allowing it to reach the oxidized trench 76 and hence fully isolate the central through-element 40; the transversal width thereof is generally higher than that of the fine blind trench 72.

To avoid that an over-engraving damages the isolating oxide of the filled fine trench 76, an advantageous variant, illustrated in FIG. 15, consists in stopping the hollowing out of the groove 78 a little before reaching the filled thin trench 76 then completing the engraving by a more selective chemical etching, illustrated in dotted line in FIG. 15, this selective etching essentially attacking the metallic substrate 10 but very little the oxide of the filled thin trench 76.

However, given the engraving depth tolerances between the edge and the center of a same wafer carrying a very large number of distinct components, certain places may be engraved more deeply than others.

Figure 16:
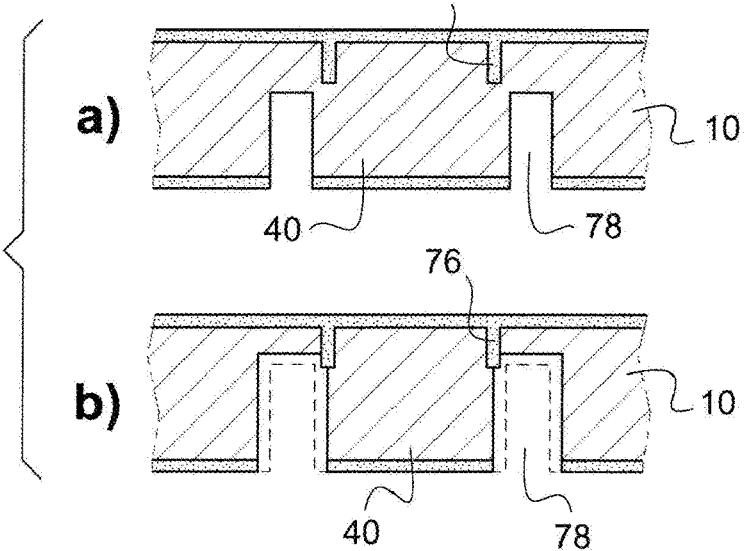

To address this drawback, and to avoid a substantial over-engraving that would excessively widen the desired dimensions, in particular in the lateral direction, it is possible, as illustrated in FIG. 16, to laterally offset the engraving of the groove 78 with respect to the position of the filled thin trench 76.

This offset in the lateral direction may be made either towards the inside or, as illustrated in FIG. 16(*a*), towards the outside, wherein the depth of the engraved groove 78 can be lower than, equal to or higher than the level of the bottom of the filled thin trench 76 located opposite.

Then, as illustrated in dotted line in FIG. 16(*b*), an isotropic, chemical or physical, engraving of the metal, propagating in all the directions makes it possible, in all the configurations, to reach the oxide of the filled trench 76 and to electrically isolate the central through-portion 40 with respect to the remainder of the substrate. The depth of the isotropic engraving of the metal is typically of the order of 15 to 20 µm.

Indeed, the tolerances of alignment between front face and rear face of a same wafer are very homogeneous and very low (typically from 1 to 5 µm) whatever the position of the component on the wafer, which reduces the required depth of isotropic engraving.

The advantage of this latter variant is its reduced sensitivity to the engraving depth tolerances, because it is sufficient to reach a minimum proximity with respect to the oxide of the filled thin trench 76 to compensate for the size variations linked to the manufacturing tolerances.

Generally, and whatever the embodiment variant implemented, it will be noted that the isolating oxide layer present on each face of the substrate has no longer any function, neither electric nor mechanical—unlike the structures of the prior art such as those illustrated in FIGS. 3 and 4. From then on, this oxide layer may be fully or selectively engraved to make the metal at the surface of the substrate exposed. The exposed metal can be used for various purposes such as electrical contact with the substrate, bonding of the piece made on another element of the device, integration of an integrated circuit chip, etc.

FIGS. 17*a*, 17*b*, 18*a* and 18*b* are cross-sectional views illustrating, according to two different implementation possibilities, a variant of the method of FIGS. 13 to 16, at the stage of the method in which the blind thin trench 72 and the groove 78 have just been engraved (FIGS. 17*a* and 17*b*) and after completion of the step of controlled oxidation of the substrate material, respectively.

In this variant, in which the thin trench 72 engraved on one face is offset with respect to the groove 78 engraved on the other face, the electrical isolation between the engravings (and hence between the central islet and the remainder of the substrate) is established by an oxidation 76 of the gap between the trench 72 and the groove 78. This may be made either by engraving of the blind trench 72 and of the groove 78 either in an offset configuration with vertical overlapping (FIG. 17*a*), or in an offset configuration with vertical proximity (FIG. 17*b*).

The order of engraving of the blind trench 72 and of the groove 78 on one face then on the other is indifferent. The trench 72 and the groove 78 may be offset in different directions (inward offset, outward offset, overlapping offset). Each of the blind trench 72 and the groove 78 defines a respective islet 40*a*, 40*b* and these two islets, when they will be electrically isolated together from the remainder of the substrate, will form the central conductive element 40 of the feedthrough.

The engraving depth of the blind trench 72 and of the groove 78 must be sufficient on either side to define a very fine separation between both (whose size may vary, typically but without limitation, between 0.5 µm and 25 µm).

The offset defining the gap between the blind trench 72 and the groove 78 will be thin enough so that this gap is fully oxidized (as in 76 in the figures), hence becoming electrically isolating.

Figure 18A:
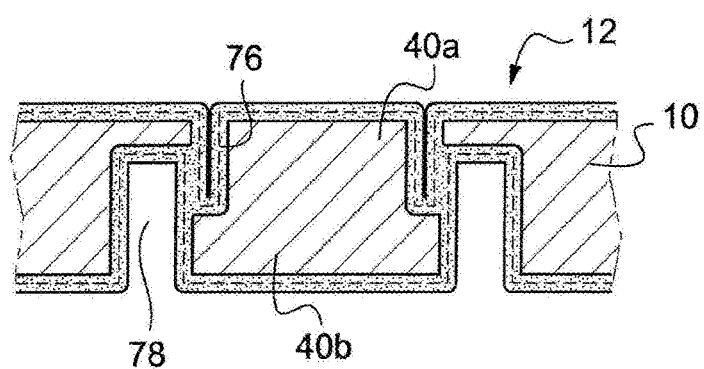
FIGS. 18a and 18b are homologous to FIGS. 17a and 17b, after completion of the step of controlled oxidization of the substrate material.
Figure 18B:
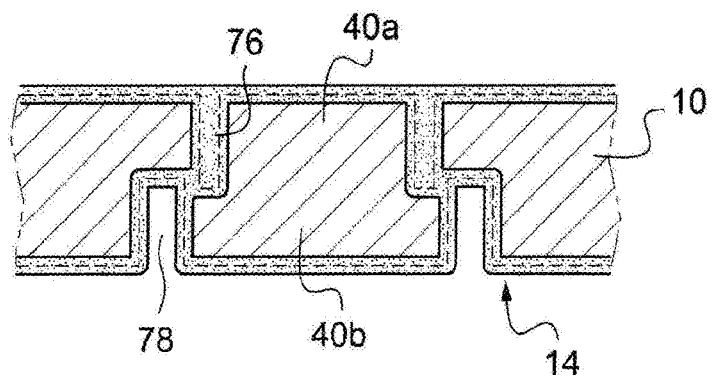

In the implementation illustrated in FIG. 18*b*, one at least of the blind trench 72 and of the groove 78, preferably the trench 72 as illustrated in FIGS. 18*a* and 18*b*, may be narrow enough so that its volume is fully filled by the oxide during the thermal oxidation (as in 76 in FIG. 18*b*). If this is not the case (as illustrated in FIG. 18*a*), the free residual volume of the oxidized trench(es) may be filled—or not—by the later deposition of another material, so as to rigidify the structure.

Figure 17A:
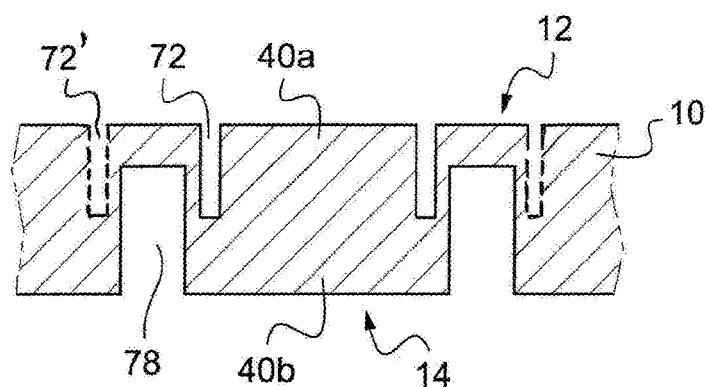
FIGS. 17a and 17b are cross-sectional views illustrating, according to two respective possibilities of implementation, a variant of the method of FIGS. 13 to 16, at the step of the method in which the blind trenches have just been engraved.
Figure 17B:
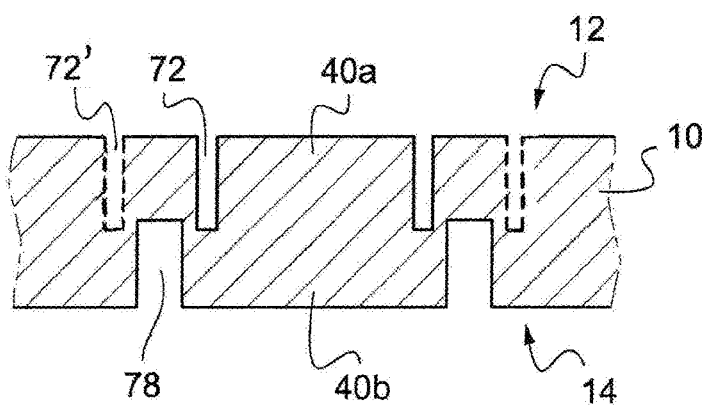

Finally, to compensate for any defect of alignment of the engraving of one face with respect to the other, which would generate on one side a too thick metal wall for a complete oxidation of the latter, and on the other side a too thin or non-existent metal wall, alignment compensation means may be provided by making on one face a set of two concentric thin trenches 72, 72' (as illustrated in FIGS. 17*a* and 17*b*), surrounding each groove on the opposite face. That way, there will always be on either side of the central islet at least one metal wall having the desired dimensions, whatever the tolerances of alignment between the respective etchings of each face.

Having thus described the invention of the present application in detail and by reference to embodiments thereof, it will be apparent that modifications and variations are possible without departing from the scope of the invention defined in the appended claims as follows:

I claim:

1. A method of making a hermetic and electrically isolating feedthrough for a passage of an electrical connection through a metal wall of an electrical device, comprising:
   a) obtaining a metallic substrate whose thickness corresponds to a transverse size of the wall comprising the feedthrough to be made;
   b) partially thinning down a region of the substrate, at least in a zone of isolation of an area of the feedthrough to be made;
   c) shaping an islet into the substrate material, by hollowing out from the substrate material a through-trench extending transversally through the substrate thickness, right through the partially thinned region, said through-trench extending transversally over a whole periphery of the islet with an exception of radial bridges of material holding the islet mechanically secured to a remainder of the substrate;
   d) performing a controlled oxidation of the substrate material, including an oxidation of lateral walls of the trench up to i) complete filling of a free inner volume of the trench by growth of an oxide in this free inner volume, and ii) complete oxidation of the material of the radial bridges;
   e) making at least one contact arrangement for said electrical connection directly on the islet; and
   f) terminating the method without having performed a general thinning down of the substrate in addition to the partially thinning down of the region of the substrate.

2. The method of claim 1, comprising:
   hollowing out, from a first face of the substrate, a blind trench extending transversally through a fraction of the substrate thickness; and,
   the partially thinning down further comprising thinning down the substrate, from a second face opposite to the first face and facing the blind trench, over a sufficient depth to reach the blind trench and make the blind trench through-going.

3. The method of claim 1, wherein at step b), the partially thinning down is made with a width varying as a function of a depth, increased near a first face of the substrate and reduced toward a second, opposite face of the substrate, near the radial bridges.

4. A method of making a hermetic and electrically isolating feedthrough for a passage of an electrical connection through a metal wall of an electrical device, comprising:
   a) obtaining a metallic substrate whose thickness corresponds to a transverse size of the wall comprising the feedthrough to be made;
   b) shaping an islet into the substrate material, by hollowing out, from a first face of the substrate, at least one blind trench extending transversally through a fraction of the substrate thickness,
      said blind trench extending laterally over a whole periphery of the islet;
   c) performing a controlled oxidation of the substrate material, including an oxidation of lateral walls of the trench up to filling all or part of a free inner volume of the trench by growth of a oxide in this free inner volume;
   d) hollowing out a peripheral groove from the substrate, from a second face opposite to the first face, said peripheral groove having radially such width and position that the groove, once hollowed out, reaches the oxidized blind trench facing it, hence electrically isolating the islet from a remainder of the substrate; and
   e) making at least one contact arrangement for said electrical connection directly on the islet; and
   f) terminating the method without having performed a general thinning down of the substrate.

5. The method of claim 4, wherein:
   the position of the hollowed-out peripheral groove shows a transverse offset of a peripheral groove contour with respect to a contour of the oxidized blind trench facing it, and
   after the groove has been hollowed out, a non-oxidized material of the substrate is selectively isotropically engraved up to exposing an oxidized material of the trench, so as to hence electrically isolate the islet from a remainder of the substrate.

6. A method of making a hermetic and electrically isolating feedthrough for a passage of an electrical connection through a metal wall of an electrical device, comprising:
   a) obtaining a metallic substrate whose thickness corresponds to a transverse size of the wall comprising the feedthrough to be made;
   b) shaping a first islet into the substrate material, by hollowing out, from a first face of the substrate, at least one blind trench extending transversally through a fraction of the substrate thickness,
      said blind trench extending laterally over a whole periphery of the first islet;
   c) shaping a second islet into the substrate material, by hollowing out, from a second face of the substrate, opposite to the first face, at least one blind groove extending transversally through a fraction of the substrate thickness,
      said blind groove extending laterally over a whole periphery of the second islet, a contour of the second islet being close to a contour of the first islet;
   d) performing a controlled oxidation of the substrate material, including an oxidation of walls of the trench and of the groove through such a depth that, laterally, an oxidized area of the trench reaches an oxidized area of the groove, hence electrically isolating the first and second islets from a remainder of the substrate;
   e) making a contact arrangement for said electrical connection directly on one and/or the other of the first and second islets; and
   f) terminating the method without having performed a general thinning down of the substrate.

7. The method of claim 6, wherein the shaping comprises hollowing out, from said first face, at least a set of two concentric blind trenches laterally surrounding each respective blind groove on said second, opposite face.

8. The method of claim 1, wherein the material of the metallic substrate and of a metal through-element is a material that is biocompatible, biostable and resistant to corrosion.

9. The method of claim 8, wherein the biocompatible, biostable and corrosion-resistant material is titanium.

10. The method of claim 1, wherein the electrically isolating material of the peripheral lateral layer is an oxide of the material of the metallic substrate and of a through-element.

11. The method of claim 1, wherein the feedthrough comprises a coupling interface comprising at least two concentric peripheral lateral layers made of an electrically isolating material.

12. The method of claim 11, wherein the feedthrough comprises a capacitor structure coupled to said electrical connection, said capacitor structure comprising three concentric lateral layers with, successively:
- a lower conductive layer formed in the substrate material, defining a first electrode for the capacitor;
- an intermediate layer made of an electrically isolating material, defining a dielectric of the capacitor; and
- an external conductive layer formed in the substrate material, defining a second electrode for the capacitor.

* * * * *